United States Patent [19]

Tóth et al.

[11] Patent Number: 4,504,481

[45] Date of Patent: Mar. 12, 1985

[54] BENZHYDRYLPIPERAZINE DERIVATIVES, PROCESS FOR THEIR PREPARATION AND PHARMACEUTICAL COMPOSITIONS CONTAINING THEM

[75] Inventors: Edit Tóth; Jozsef Torley; Eva Pálosi; Szabolcs Szeberenyi; Laszlo Szporny; Sándor Görög; István Hajdu, all of Budapest, Hungary

[73] Assignee: Richter Gedeon Vegyeszeti Gyar Rt., Budapest, Hungary

[21] Appl. No.: 565,923

[22] Filed: Dec. 27, 1983

[30] Foreign Application Priority Data

Dec. 28, 1982 [HU] Hungary ................ 4187/82

[51] Int. Cl.³ ............... A61K 31/495; C07D 295/02
[52] U.S. Cl. ........................... 514/255; 544/396
[58] Field of Search .................. 544/396; 424/250

[56] References Cited

U.S. PATENT DOCUMENTS

| | | | |
|---|---|---|---|
| 3,868,377 | 2/1975 | Raabe et al. | 544/396 |
| 3,957,790 | 5/1976 | Suzuki et al. | 544/396 |
| 4,160,099 | 7/1979 | Bodor | 544/396 |

FOREIGN PATENT DOCUMENTS

| | | | |
|---|---|---|---|
| 89077 | 5/1975 | Japan | 544/396 |
| 9854 | 11/1975 | Japan | 544/396 |

OTHER PUBLICATIONS

Chem. Abstracts, vol. 22, p. 410, article 1.
Chem. Abstracts, vol. 35, 1871(2).
Chem. Abstracts, vol. 40, 4712(5).
Chem. Abstracts, vol. 42, 1015(b).
Chem. Abstracts, vol. 47, 9548(e).
Chem. Abstracts, vol. 50, 12390(c).
Chem. Abstracts, vol. 50, 2509(i).
Chem. Abstracts, vol. 55, 17915(e).
Chem. Abstracts, vol. 55, 15413(b).
Chem. Abstracts, vol. 75, P 103682(b).
Chem. Abstracts, vol. 76, P 11 9921(k).
Chem. Abstracts, vol. 82, 16477(q).
Chem. Abstracts, vol. 90, 86062q.
Chem. Abstracts, vol. 92, 52927b.
Organische-Chemische Arzneimittel und Ihre Synonyma, Negwer, p. 960, 1978.

*Primary Examiner*—Paul M. Coughlan, Jr.
*Assistant Examiner*—Cecilia Shen
*Attorney, Agent, or Firm*—Karl F. Ross; Herbert Dubno

[57] ABSTRACT

The invention relates to new benzhydrylpiperazine derivatives of the formula (I)

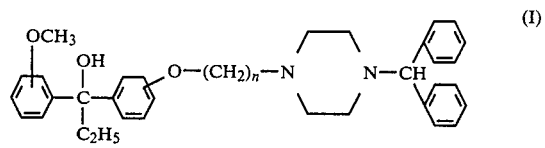

wherein n is 2 or 3, and acid addition salts thereof.

According to another aspect of the invention there are provided processes for the preparation of these compounds.

The compounds of the formula (I) are pharmacologically active. More particularly, they inhibit the microsomal monooxigenase enzyme system of liver. Pharmaceutical compositions containing them as active ingredient are also within the scope of the invention.

4 Claims, No Drawings

BENZHYDRYLPIPERAZINE DERIVATIVES, PROCESS FOR THEIR PREPARATION AND PHARMACEUTICAL COMPOSITIONS CONTAINING THEM

This invention relates to new benzhydrylpiperazine derivatives and acid addition salts thereof. More particularly, the invention concerns new benzhydrylpiperazine derivatives of the formula (I)

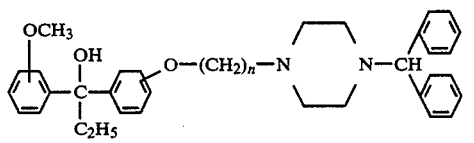

wherein n is 2 or 3, and acid addition salts of these compounds.

The invention further relates to processes for the preparation of the compounds of the formula (I) and acid addition salts thereof.

The new compounds of the formula (I) are pharmacologically active. According to a further aspect of the invention there are provided pharmaceutical compositions containing them as active ingredient.

Compounds of analogous structure are disclosed for example in the following references: C.A. 22, 410[1]; 35, 1871[2]; 40, 4712[5]; 42, P 1015 b; 47, 9548 e; 50, 12390 c; 50, 2509 i; 55, 17915 e; 55, 15413 b; 75, P 103682 b; 76, P 11 9921 k; 82, 16477 q; 90, 86062 q; 92, 52927 b. None of these citations, however, mentions any pharmaceutical activity of the disclosed compounds.

The new compounds according to the invention are pharmacologically active. More particularly, they inhibit the liver microsomal monooxygenase enzyme system, and can therefore used in therapy to inhibit or reduce the toxic effect of xenobiotic substances which are transformed into toxic, active metabolites in the liver (D. M. Jerina et al.: Science, 185, 573 (1974)), resulting in liver necrosis, blood discrasia, carcinosis. In pharmaceutical combinations the compounds according to the invention may increase the duration of the effect of other active ingredients.

The enzyme inhibiting activity of the new compounds was tested in vivo, by measuring the change of hexobarbital oxidase activity. Female Hann.-Wistar rats, each weighing 50 to 60 g. were treated orally with a single 40 mg./kg. dose of the test compound. One and 24 hours after the administration of the active ingredient, the animals were narcotized with a 60 mg./kg. i.v. dosage of hexobarbital sodium, and the time elapsed until complete wakening was measured (Noordhoek, J.: Eur. J. Pharmacol., 3, 242 (1968)). The data were recorded, and the mean values, the standard errors as well as the percentage increase with respect to the controls were calculated for each group. As a reference compound Proadiphene(2-diethylaminoethyl)-α,α-diphenyl valerate), the most effective known compound, was employed, in a dose of 100 mg./kg. The hexobarbital concentration of the plasm, measured on the instant wakening, was the same for both the treated and the control animals, and thus the increase of narcosis period was not due to a certain central nervous interaction (Jori, A. et al.: Biochem. Pharmacol., 19, 2687 (1970)). The results are shown in Table 1.

Abbreviations:

$\bar{x}$ = mean value
S.E. = standard error of the mean value
n = number of animals
The control group was treated with placebo.
A = α-ethyl-α-(2-methoxyphenyl)-4-[3-(4-benzhydryl-piperazin-1-yl)-propoxy]-benzylalcohol

TABLE 1

| Compound | Dose (mg./kg.) | Hexobarbital narcosis period in % of control | | n |
|---|---|---|---|---|
| | | 1 hour | 24 hours | |
| Control | — | 100 ± 8.3 (1) | 100 ± 11.1 (2) | 10 |
| A | 40.0 | 116 ± 6.7 | 172 ± 8.7 | 10 |
| Proadiphene | 100.0 | 241 ± 9.6 | 44 ± 5.7 | 10 |

Control ($\bar{x}$ ± S.E.) = 44.3 ± 5.67 min. (1)
47.0 ± 5.21 min. (2)

Both the increase of the narcosis period and the permanence of the effect (the compounds being effective even 24 hours after administration) indicate that the compounds of the formula (I) inhibit the biotransformation of xenobiotic agents in the liver for a long time. The effect of the new compounds provided by the invention is better than that of Proadiphene also from qualitative aspects since, in contrast to Proadiphene, the initial inhibiting effect caused by the compounds according to the invention is not followed by an increase, i.e. induction, of the activity of the microsomal enzyme system.

The enzyme inhibiting activity of the compounds of the formula (I) was further tested by determining the activity of the polysubstrate liver monooxygenase enzyme system after treatment with placebo and the compounds according to the invention, respectively. Female H.-Wistar rats weighing 50 to 60 g. each were administered a single 40 mg./kg. oral dose of the test compounds. Two hours after treatment the animals were decapitated and the livers were removed. After rinsing with a physiological saline solution at 0° C., drying and weighing, the livers were homogenized in a 0.1 molar Tris-HCl buffer (pH=7.4), containing 1.15% of potassium chloride at 0° C., centrifuged at 9000 g for 20 minutes, and the supernatant (postmitochondrial fraction) was used for further investigations. The microsomal fraction was prepared following the method developed by Cinti D. L. et al.: Biochem. Pharmacol., 21, 3249 (1972). The activity of aniline hydroxylase was determined from the velocity of p-amino-phenol formation according to Chabra R. S. et al.: Toxicol. Appl. Pharmacol. 22, 50 (1972). The activity of the aminopyrine demethylase was measured from the amount of the formaldehyde formed, according to Gourlay G. K. et al: Biochem. Pharmacol., 27, 965 (1978). The control groups were treated with placebo. The results are shown in Table 2, expressed in percentage of the control.

TABLE 2

| Compound | Aniline hydroxylase (nmoles/g. of liver/min.) | Aminopyrine demethylase (nmoles/g. of liver/min.) |
|---|---|---|
| Control | 100 ± 2.7 (1) | 100 ± 4.3 (2) |
| A | 72 ± 5.8 | 71 ± 8.1 |

Control (1) = 19.8 ± 0.53 $\bar{x}$ ± S.E.
(2) = 260.7 ± 11.2 $\bar{x}$ ± S.E.

As appears from the data of Table 2, the compounds according to the invention substantially inhibit the activity of the enzyme system responsible for biotranformation already two hours after administration.

The central nervous activities of the compounds according to the invention were examined on mice and rats with the following methods: electroshock (Swinyard, E. A., Brown, W. C., Goodman, L. S.: J. Pharmacol. Exp. Ther. 106, 319 (1952)), metrazole spasm (Everett, G. M., Richards, R. K.: J. Pharmacol. Exp. Ther. 81, 402 (1944)), thiosemicarbazide spasm (Da Venzo, J. P., Greig, M. E., Cormin, M. A.: Amer. J. Physiol. 201, 833 (1961)), strychnine spasm (Kerley, T. L., Richards, A. G., Begley, R. W., Abreu, B. B., Wesver, L. C.: J. Pharmacol. Exp. Ther. 132, 360 (1961)), nicotine spasm (Stone, C. A., Mecklenburg, K. L., Torhans, M. L.: Arch. Int. Pharmacodyn. 117, 419 (1958)), rotarod test (Kinnard, W. C., Carr, C. J.: J. Pharmacol. Expt. Ther. 121, 254 (1957)), physostigmine lethality preventing effect (Nose, T., Kojima, M.: Europ. J. Pharmacol. 10, 83 (1970)), yohimbine potentiation effect (Quinton, R. M.: Brit. J. Pharmacol. 21, 51 (1963)), and analgesic activity (Bianchi, G., Franceschini, J.: Brit. J. Pharm. Chemother. 9, 280 (1954)).

The compounds according to the invention when tested by the above methods proved completely ineffective, whereas Proadiphene exerted an anticonvulsive side effect (H. Ippen: Index Pharmacorum (1970), 40S 3.1).

The acute toxicity of the compounds having the formula (I) was tested on H-Wistar rats of both sexes, each weighing 160 to 180 g. The compounds were administered in a single 500 mg./kg. oral dose. The adnimals were observed for 14 days. The results are set forth in Table 3.

TABLE 3

| Compound (500 mg./kg. p.o.) | Perished animals (%) | n |
|---|---|---|
| A | 0 | 10 |
| Proadiphene | 90 | 10 |

The data show that the toxicity of the instant compounds is considerably lower than that of Proadiphene, accordingly, their therapeutic index is much more favorable.

The new compounds according to the invention are prepared for example by (a) reacting a propiophenone of the formula (II)

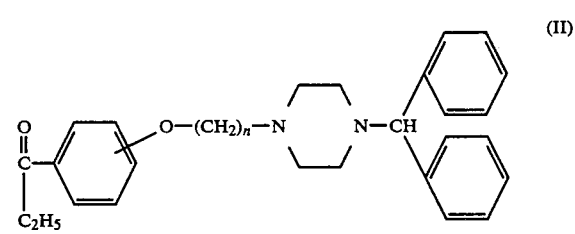

wherein n has the same meaning as defined above, with an organometallic compound of the formula (III)

wherein M is an alkali metal, preferably lithium, sodium or potassium, or an MgX group, in which X is halogen; or (b) reacting a compound of the formula (IV)

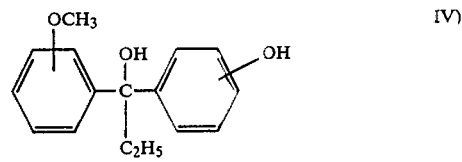

preferably in form of an alkali metal or quaternary ammonium phenolate thereof, with an amine of the formula (V)

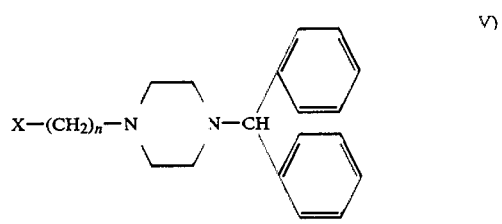

wherein
n is as defined above, and
X stands for halogen, alkylsulfonyloxy or arylsulfonyloxy,
or a salt thereof, preferably in the presence of an acid binding agent; or (c) reacting a propiophenone of the formula (VI)

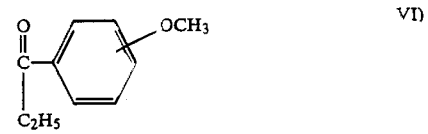

with a Grignard compound of the formula (VII)

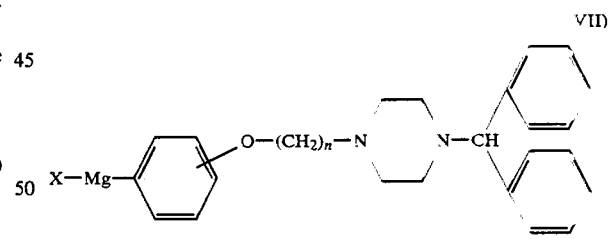

wherein
n has the same meaning as defined above, and
X is halogen; or (d) reacting a compound of the formula (VIII)

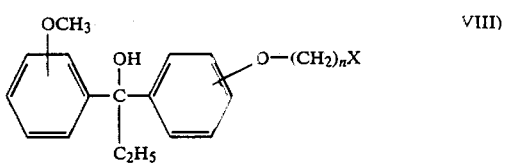

wherein
n is as defined above, and
X is halogen, with 1-benzhydryl-piperazine, preferably in the presence of an acid binding agent, and if desired, converting any of the products obtained by process variants (a) to (d) into their acid addition salts.

According to a preferred embodiment of process variant (a) propiophenone of the formula (II) is reacted with an organometallic compound of the formula (III), preferably with a suitably substituted phenyl magnesium chloride or bromide or a suitably substituted phenyl lithium in a dry inert organic solvent. The reaction is preferably carried out in an aprotic organic solvent, e.g. in an aliphatic ether such as diethyl ether, di-n-butyl ether or diethylene glycol dimethyl ether, an alicyclic ether such as tetrahydrofurane, dioxane, an aliphatic or aromatic hydrocarbon such as ligroin, benzene, toluene, xylene, dimethyl sulfoxide or hexamethyl phosphorus amide, or a mixture of these solvents. The organometallic compound is used in an at least equimolar amount. The reaction is preferably performed in an inert gas atmosphere, e.g. in nitrogen or argon. The reaction temperature may range from −60° C. up to the boiling point of the solvent, and preferably is between −30° C. and 100° C. When the reaction is complete, the reaction mixture is decomposed, preferably with an aqueous ammonium chloride solution, and the obtained compound of the formula (I) is separated. The product can be purified by known techniques, e.g. by distillation or crystallization.

According to process variant (b) a compound of the formula (IV), preferably in form of its alkali metal or quaternary ammonium phenolate, is condensed with a compound of the formula (V). Preferably a mesylate, tosylate, bromide or more preferably chloride of the formula (V) is used in the reaction. The reaction is preferably carried out in an inert organic solvent, in the presence of an acid binding agent, under anhydrous conditions or in a mixture of water and an organic solvent. As organic solvents for example esters such as ethyl acetate, ethers such as dioxane, tetrahydrofurane or diethyl ether, hydrocarbons such as ligroin, benzene, toluene or xylene, halogenated hydrocarbons such as chloroform, chlorobenzene, acid amides such as dimethyl formamide, ketones such as acetone, methyl ethyl ketone or methyl isobutyl ketone, alcohols such as ethanol, propanol, etc. are employed. Compounds of the formula (IV) can be converted into their phenolates by methods known in the art, e.g. with alkali metal alcoholates, amides, hydrides, hydroxides, carbonates or quaternary ammonium compounds. Preferred acid binding agents include inorganic and tertiary organic bases, e.g. sodium hydroxide, potassium hydroxide, potassium carbonate, triethyl amine, pyridine, etc. The reaction is optionally performed in the presence of a catalyst. As a catalyst for example alkali metal halides, preferably alkali metal iodides, may be used. The reaction temperature may be varied within a wide range, and preferably is between 20° C. and the boiling point of the solvent.

According to process variant (c) the Grignard compounds of the formula (VII), in which X preferably represents a bromine atom, are preferably reacted with an at least equimolar amount of the propiophenone of the formula (VI), in a dry inert organic solvent, similarly to process variant (a).

According to process variant (d) compounds of the formula (VIII), in which X preferably represents chlorine or bromine, are reacted with 1-benzhydryl-piperazine. The reaction is preferably carried out in an organic solvent, in the presence of a base suitable for binding the acid formed in the reaction. As a solvent for example hydrocarbons such as ligroin, benzene, toluene, halogenated hydrocarbons such as chloroform, ethers such as dioxane, alcohols such as ethanol, esters such as ethyl acetate, acid amides such as dimethyl formamide, ketones such as acetone, methyl isobutyl ketone, or mixtures of these solvents are employed. Preferred acid binding agents include inorganic and tertiary organic bases, but the excess of 1-benzhydryl-piperazine may also be used for this purpose. The reaction is performed between 20° C. and the boiling temperature of the solvent employed. When the reaction is complete, the product is isolated. The reaction mixture may for example be poured onto water, and the product can be isolated by solvent extraction. The organic phase is washed to halogen-free with water, dried and evaporated. The crude product can be purified for example by crystallization.

If desired, the compounds of the formula (I) can be converted into their acid addition salts by methods known in the art. The acid addition salts can be prepared by means of inorganic or organic acids, e.g. hydrogen halides such as hydrochloric acid, hydrogen bromide, etc., sulfuric acid, phosphoric acids, formic acid, acetic acid, propionic acid, oxalic acid, glycolic acid, maleic acid, fumaric acid, tartaric acid, succinic acid, ascorbic acid, citric acid, malic acid, salicylic acid, lactic acid, benzoic acid, cinnamic acid, asparaginic acid, glutaminic acid, N-acetyl-asparaginic acid, N-acetyl-glutaminic acid, alkylsulfonic acids such as methanesulfonic acid, arylsulfonic acids such as p-toluenesulfonic acid, etc.

According to a preferred embodiment, the corresponding acid is added to a solution of a compound of the formula (I) in an inert solvent, e.g. ethanol, and the salt formed is precipitated, preferably with a water-immiscible organic solvent such as diethyl ether.

The starting compounds are known or can be prepared by methods known in the art. The ketones of the formula (II) or (VI) can for example be synthetized by the Friedel-Crafts ketone synthesis (G. A. Olah: Friedel-Crafts and related reactions, III/1, Ed.: Interscience Publishers 1964, pp. 1–63).

The compounds of the formulae (III) and (VII) are for example prepared from the corresponding aryl halides by known techniques (M. S. Kharash et al.: Grignard reactions of nonmetallic substances, Ed.: Prentice-Hall. Inc. (1954) pp. 5–90), while the alkali metal-organic compounds can be prepared following the method disclosed in Houben-Weyl: Methoden der Organischen Chemie, XIII/1, pp. 134–159 and 389–405 (1970).

The compounds of the formulae (IV) and (VIII) can for example be synthesized from the corresponding propiophenones by reaction with the corresponding Grignard reactants, following well known techniques (see e.g. M. S. Kharash et al.: Grignard reactions of nonmetallic substances, Ed.: Prentice-Hall Inc. (1954) 138–143).

The pharmacologically active compounds of the formula (I) can be used in therapy in the form of pharmaceutical compositions, which are formulated as preparations suitable for oral, rectal and/or parenteral administration. For oral administration tablets, dragées capsules are prepared. The oral formulations contain as a vehicle e.g. lactose or starch, as an excipient or a granulation aid e.g. gelatine, carboxymethyl cellulose sodium, methyl cellulose, polyvinyl pyrrolidone or starch gum, as a disintegrating substance e.g. potato starch or formaldehyde casein, etc. The formulations may contain adhesives and lubricants such as talc, colloidal silica, stearin, calcium or magnesium stearate, etc. as well.

Tablets are prepared for example by wet granulation and subsequent pressing. A mixture of the active ingredient and the vehicle and optionally a portion of the disintegrating agent are granulated with an aqueous, alcoholic or aqueous-alcoholic solution of the excipients in a suitable equipment, and the granulate is dried. The remaining portion of the disintegrating substance, lubricant, antiadhesive or optional further additives is then added to the granules, and the mixture is pressed to tablets. If desired, the tablets are prepared with a dividing line, which facilitates administration. Tablets can be prepared also from a mixture of the active ingredient and suitable additives by direct pressing.

If desired, the tablets can be converted into dragées, using protecting, flavoring agents and pigments generally known for the preparation of pharmaceutical compositions, e.g. sugar, cellulose derivatives (methyl or ethyl cellulose, carboxymethyl cellulose sodium, etc.), polyvinylpyrrolidone, calcium phosphate, calcium carbonate, food pigments, food oil varnishes, aroma substances, iron oxide pigments, etc.

Capsules are prepared by filling a mixture of the active ingredients and additives into suitable capsules.

For rectal administration the compositions are formulated as suppositories, which contain in addition to the active ingredient as carrier mass, called adeps pro suppository. Suitable carriers include vegetable fats, e.g. hardened vegetable oils, triglycerides of fatty acids having from 12 to 18 carbon atoms, preferably Witepsol (a registered trade mark). The active ingredient is homogeneously distributed in the melted carrier mass, and suppositories are prepared by casting.

For parenteral administration injectable preparations are prepared. To prepare an injectable solution the active ingredient is dissolved in distilled water and/or various organic solvents, e.g. glycol ethers, optionally in the presence of dissolution aids, e.g. polyoxyethylene sorbitane monolaurate, monooleate or monostearate (Tween 20, Tween 60, Tween 80). The injectable solutions may contain also various additives, e.g. preserving agents such as benzyl alcohol, p-oxy-benzoic acid methyl or propyl ester, benzalkonium chloride or phenyl mercuri borate, etc., antioxidants such as ascorbic acid, tocopherol, sodium pyrosulfate and optionally complexing agents to bind metal traces such as ethylene diamine tetraacetate, buffers to adjust the pH and optionally local anaesthetics such as lidocaine. The injectable solutions are filtered, filled into ampoules and sterilized. The daily dose, depending on the state of the patient, varies between 1.0 and 200.0 mg./kg., preferably 2.0 and 40.0 mg./kg., which is preferably administered in more smaller dose units.

The invention will be further illustrated by the following Examples but it is not intended to limit the scope of the invention to the Examples.

EXAMPLE 1

α-Ethyl-α-(2-methoxyphenyl)-4-[3-(4-benzhydryl-piperazin-1-yl)-propoxy]-benzyl alcohol To a Grignard reactant prepared from 1.26 g. of magnesium turnings and 9.3 g. of 2-bromo-anisole in 29 ml. of dry tetrahydrofurane a solution of 11.1 g. of 4-[3-(4-benzhydryl-piperazin-1-yl)-propoxy]-propiophenone in 40 ml. of dry tetrahydrofurane is added dropwise, with stirring under slight reflux. The reaction mixture is slightly boiled for further 60 minutes. After cooling it is decomposed with a 10% aqueous ammonium chloride solution, tetrahydrofurane is distilled off under reduced pressure, and the residue is extracted with ether. The ethereal phases are combined, washed to neutral with water, and dried over anhydrous magnesium sulfate. Ether is distilled off under reduced pressure. Crystallization of the residue from a mixture of n-heptane and ethanol yields 9.1 g. of the named compound, melting at 99° to 101° C.

Analysis for $C_{36}H_{42}N_2O_3$: Calculated: C 78.51%, H 7.69%, N 5.09%; Found: C 78.63%, H 7.80%, N 4.93%.

To a solution of the above base in dry ethanol an ethanolic solution of two equivalents of maleic acid is added, and the mixture is diluted with dry ether. The bis-hydrogen maleate crystals are filtered off and dried. Melting point: 143° to 145° C.

EXAMPLE 2

5.2 g. of α-ethyl-α-(4-hydroxyphenyl)-2-methoxy-benzyl alcohol, 6.6 g. of 3-(4-benzhydrylpiperazin-1-yl)-propyl chloride, 4.2 g. of dry potassium carbonate and 0.25 ml. of a 40% aqueous tetrabutyl ammonium hydroxide solution are boiled in 52 ml. of methylisobutyl ketone for 5 hours, with stirring, whereupon the solvent is distilled off under reduced pressure. To the residue water is added and it is extracted with benzene. The benzene phases are combined, shaken with a 5% aqueous potassium hydroxide solution, and washed to neutral with water. After drying over anhydrous calcium carbonate, benzene is distilled off in vacuo, and the residue is crystallized from a mixture of hexane and ethanol to yield 8.9 g. of a product, which has the same physical characteristics as the product of Example 1.

EXAMPLE 3

6.7 g. of α-ethyl-α-[4-(3-chloropropoxy)phenyl]-2-methoxy-benzyl alcohol, 4.2 g. of anhydrous potassium carbonate, 5.0 g. of 1-benzhydrylpiperazine and 0.17 g. of potassium iodide in 70 ml. of acetone are boiled with stirring for 12 hours. The reaction mixture is cooled, filtered, and the filtrate is evaporated under reduced pressure. The residue is dissolved in ether. The ethereal solution is washed to neutral with water, dried over anhydrous magnesium sulfate and evaporated in vacuo. Crystallization of the residue from a mixture of n-hexane and ethanol yields 6.9 g. of a product, which has the same physical characteristics as the product of Example 1.

To a solution of the above base in dry ethanol an ethanolic solution of two equivalents of citric acid are added, and the solution is evaporated under reduced pressure. The residue is crystallized from dry ether. Melting point of bis-dihydrogen citrate: 53° C.

EXAMPLE 4

To 100 ml. of a 0.4 molar solution of 4-[3-(4-benzhydryl-piperazin-1-yl)-propoxy]-phenyl magnesium bromide in tetrahydrofurane a solution of 6.5 g. of 2-methoxy-propiophenone in 30 ml. of dry tetrahydrofurane is added dropwise, at 20° C. The reaction mixture is boiled for two additional hours. After cooling, the reaction mixture is poured onto a saturated aqueous ammonium chloride solution, and the organic phase is separated. The aqueous phase is extracted with benzene.

The solvent phases are combined, washed with a saturated aqueous sodium chloride solution and dried over anhydrous sodium sulfate. The solvent is distilled off under reduced pressure. The residue is triturated with n-hexane, the solid product is filtered off and recrystallized from a mixture of n-heptane and ethanol. 9.3 g. of a product is obtained, which has the same physical characteristics as the product of Example 1.

The bis-hydrogen fumarate prepared from the above base on the analogy of Example 1 melts at 161° to 163° C.

EXAMPLE 5

The compounds according to the invention can for example be converted into the following pharmaceutical compositions.

TABLETS

Composition of a single tablet:

| | |
|---|---|
| active ingredient | 100.0 mg. |
| lactose | 184.0 mg. |
| potato starch | 80.0 mg. |
| polyvinyl pyrrolidone | 8.0 mg. |
| talc | 12.0 mg. |
| magnesium stearate | 2.0 mg. |
| ultraamylopectin | 12.0 mg. |
| aerosil (colloidal silica) | 2.0 mg. |

From the above ingredients 400-mg. tablets are prepared by wet granulation and subsequent pressing. Active ingredient: α-ethyl-α-(2-methoxyphenyl)-4-[3-(4-benzhydryl-piperazin-1-yl)-propoxy]-benzylalcohol

DRAGÉES

Tablets as described above are coated with a coating prepared from sugar and talc in a known manner. Dragées are polished with a mixture of bee wax and carmauba wax. Weight of a dragée: 500.0 mg.

SUPPOSITORIES

Composition of a suppository:

| | |
|---|---|
| active ingredient | 100.0 mg. |
| lactose | 200.0 mg. |
| basic substance (e.g. Witepsol H) | 1700.0 mg. |

The basic substance is melted and then cooled to 35° C. The active ingredient is thoroughly blended with the lactose, and the mixture is homogenized in the basic substance in a homogenizator. The obtained mass is filled into cool moulds. One suppository weights 2000 mg. Active ingredient: α-ethyl-α-(2-methoxyphenyl)-4-[3-(4-benzhydryl-piperazin-1-yl)-propoxy]-benzyl alcohol

CAPSULES

Composition of a capsule:

| | |
|---|---|
| active ingredient | 50.0 mg. |
| lactose | 100.0 mg. |
| talc | 2.0 mg. |
| potato starch | 30.0 mg. |
| cellulose (microcrystalline) | 8.0 mg. |

The active ingredient is thoroughly admixed with the additives, the mixture is passed through a 0.32-mm. sieve, and filled into hard gelatine capsules No. 4. Active ingredient: α-ethyl-α-(2-methoxyphenyl)-4-[3-(4-benzhydryl-piperazin-1-yl)-propoxy]-benzyl alcohol.

We claim:

1. A benzhydryl-piperazine compound of the formula (I)

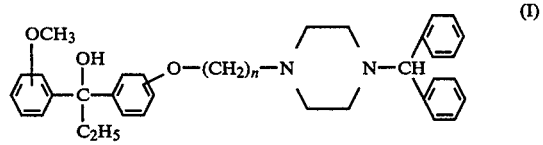

wherein n is 2 or 3, or an acid addition salt thereof.

2. α-Ethyl-α-(2-methoxyphenyl)-4-[3-(4-benzhydryl-piperazin-1-yl)-propoxy]-benzyl alcohol or an acid addition salt thereof.

3. A pharmaceutical composition containing a benzhydrylpiperazine compound of the formula (I) as claimed in claim 1, wherein n has the same meaning as defined in claim 1, or a pharmaceutically acceptable acid addition salt thereof, together with a pharmaceutically acceptable carrier and/or auxiliary substance.

4. A method of inducing the polysubstrate liver microsomal monooxygenase system of a susceptible subject which comprises administering an effective amount of a compound as defined in claim 1.

* * * * *